United States Patent
Hutton

(10) Patent No.: US 6,612,997 B1
(45) Date of Patent: *Sep. 2, 2003

(54) COLLECTION CONTAINER ASSEMBLY

(75) Inventor: Norman J. Hutton, Franklin Lakes, NJ (US)

(73) Assignee: Becton, Dickinson and Company, Franklin Lakes, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/148,668

(22) Filed: Sep. 4, 1998

Related U.S. Application Data

(60) Provisional application No. 60/058,694, filed on Sep. 12, 1997.

(51) Int. Cl.[7] .................................................. A61B 5/00
(52) U.S. Cl. ........................ 600/573; 604/317; 422/102
(58) Field of Search .................................. 604/317, 403, 604/411, 415, 318, 319, 322, 326, 327, 331; 600/573, 576, 577, 583, 574, 575, 578–582; 422/99, 101, 102; 73/863.21, 863.23, 864.91; 206/361, 363, 438

(56) References Cited

U.S. PATENT DOCUMENTS

| | | | |
|---|---|---|---|
| 3,851,817 A | * 12/1974 | Buck | ........................ 494/14 |
| 4,335,730 A | 6/1982 | Griffin | |
| 4,361,155 A | 11/1982 | Anastasio | |
| 4,399,808 A | * 8/1983 | Frissora et al. | ............. 126/583 |
| 4,483,616 A | 11/1984 | Liston et al. | |
| 4,578,588 A | 3/1986 | Galkin | |
| 4,980,129 A | 12/1990 | Columbus | |
| 5,096,062 A | 3/1992 | Burkardt et al. | |
| 5,167,929 A | 12/1992 | Korf et al. | |
| 5,236,604 A | 8/1993 | Fiehler | |
| 5,454,958 A | 10/1995 | Fiehler | |
| 5,456,887 A | 10/1995 | Calvo et al. | |
| 5,458,854 A | 10/1995 | Burns | |
| 5,511,558 A | * 4/1996 | Shepard et al. | ............. 604/573 |
| 5,533,518 A | 7/1996 | Vogler | |
| 5,536,476 A | 7/1996 | Baxter | |
| 5,634,474 A | * 6/1997 | Grippi | ........................ 600/573 |
| 5,786,228 A | * 7/1998 | Charlton | ..................... 600/573 |
| 5,830,154 A | 11/1998 | Goldstein et al. | |

* cited by examiner

*Primary Examiner*—Weilun Lo
*Assistant Examiner*—Mital Patel
(74) *Attorney, Agent, or Firm*—Nanette S. Thomas, Esq.; Scott J. Rittman, Esq.

(57) ABSTRACT

The present invention is a collection container assembly comprising a container having a wall space between the inner and outer wall of said tube whereby the external dimensions of the container are substantially the same as a standard-sized blood collection tube but with a reduced internal volume.

5 Claims, 4 Drawing Sheets

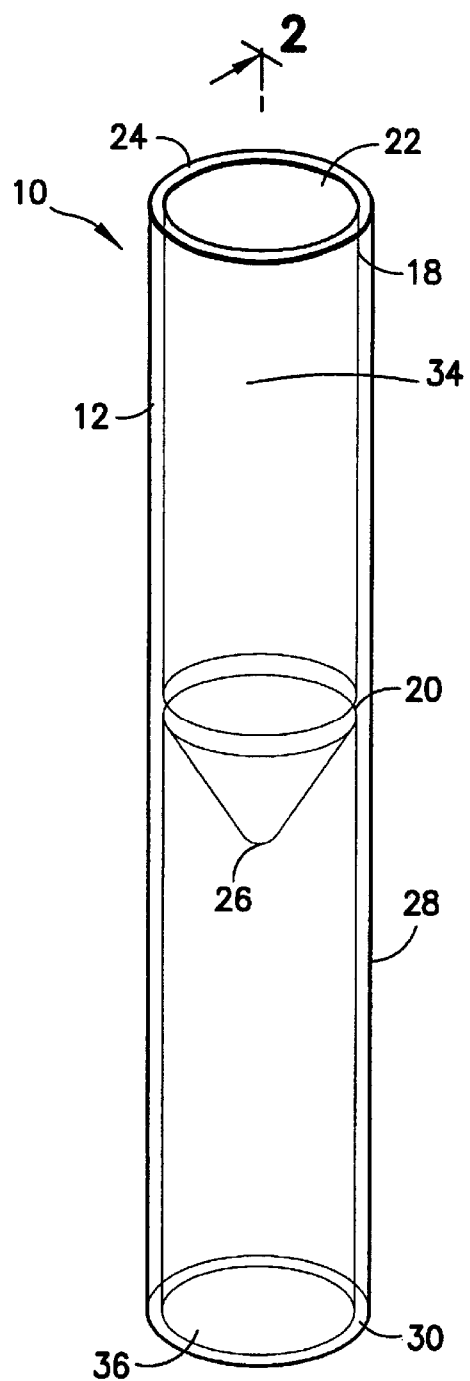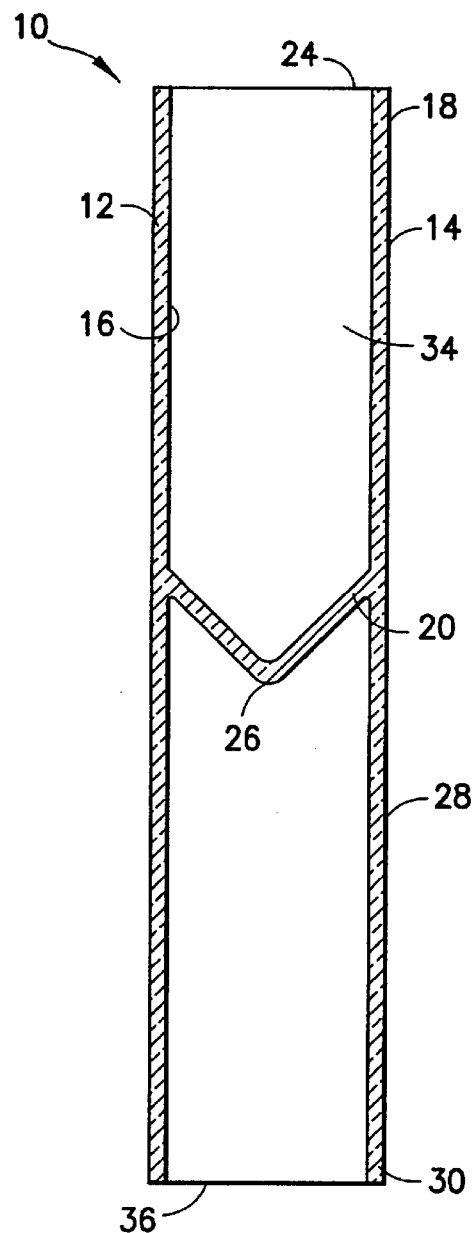
FIG. 1
PRIOR ART
FIG. 2
PRIOR ART

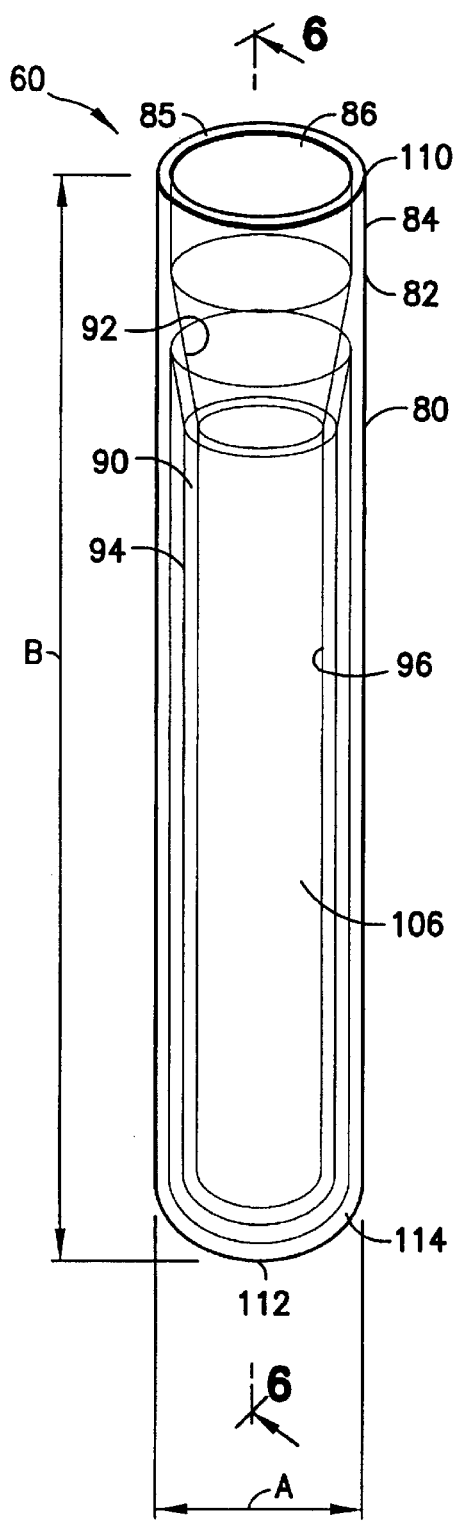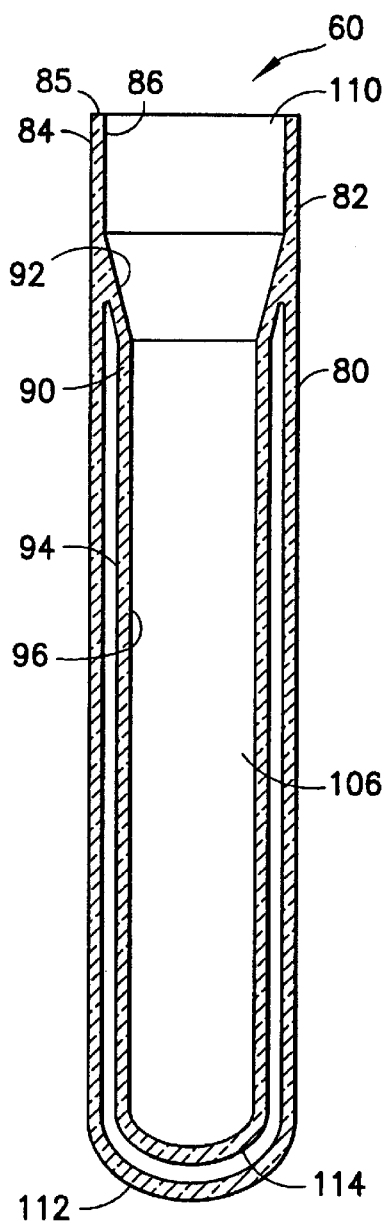
FIG.5
FIG.6

COLLECTION CONTAINER ASSEMBLY

This application claims benefit of provisional application Ser. No. 60/058,694 filed Sep. 12, 1997.

BACKGROUND OF THE INVENTION

1. Field of the Invention

This invention relates to a specimen collection container assembly and more particularly to a collection container for collecting biological fluid specimens where a small quantity of fluid may be collected and retained in the container while maintaining a container size sufficient to be easily accommodated and/or compatible with standard clinical equipment and instrumentation.

2. Description of Related Art

Blood samples and other biological fluid specimens are routinely taken and analyzed in hospital and clinical situations for various medical purposes. Collection, handling and testing of these samples typically requires the use of various medical testing instruments. As the blood and fluid specimens are usually collected in a standard sized collection tube, the medical instruments used to test the samples are designed to accommodate these standard sized collection tubes.

Conventional blood collection tubes used in most clinical situations are elongated cylindrical containers having one end closed by a semi-spherical or rounded portion and an opposed open end. The open end may be sealed by a resilient cap or stopper. The tube defines a collection interior which collects and holds the blood sample. The most common size of these blood collection tubes are designed to accommodate approximately 6–10 ml of blood or other biological fluid samples. Illustrative of such blood collection tubes is the VACUTAINER® brand blood collection tube sold by Becton, Dickinson and Company, 1 Becton Drive, Franklin Lakes, N.J. (registered trademark of Becton, Dickinson and Company).

A phlebotomist or other medical technician typically obtains a specimen of the patient's blood in the tube by techniques well known in the art. The tube is then appropriately labeled and transferred from the site of collection to a laboratory or other location where the contents of the tube are analyzed. During collection and analysis the tube may be supported by various medical instruments. The plasma or serum derived therefrom is processed and analyzed either manually, semi-automatically or automatically. In some cases, the specimen must first be dispensed from the collection tube to a sample test tube or cuvette.

In certain situations it is only necessary to obtain a small quantity of blood or other biological fluid specimens. These situations may include pediatric, or geriatric patients and other instances where large blood samples are not required. Small quantities of blood cannot be easily collected in standard collection tubes as described above because the sample level in such containers would not be adequate for retrieval prior to analysis. Such small quantities of fluids also have a tendency to significantly evaporate when stored in larger containers, thus concentrating the chemical and enzymatic constituents therein. This may result in erroneous analytical results and could possibly affect the diagnosis and treatment given the patient. Therefore, it is desirable to employ small-volume containers which substantially inhibit evaporation for the storage and delivery of minute fluid samples in the laboratory.

Various specimen containers such as those incorporating a "false bottom" have been proposed to achieve decreased volume capacity in conjunction with standard external dimensions. However, these various specimen containers are not compatible with standard clinical equipment and instrumentation due to their design. In particular, these specimen containers have false bottoms with a generally flat, planar bottom end and a circular shaped opening.

Other specimen containers include partial-draw tubes which have standard external dimensions with partial evacuation so that blood fills only a portion of the internal volume. However, partial-draw tubes exhibit a reduction in the draw rate of a sample which reduces the collection efficiency of such tubes. In addition, partial-draw tubes may result in an inconsistent fill volume which may alter test results. Furthermore, it is difficult to determine accurate sample quantities with such partial-draw tubes because the slow rate of sample draw is not consistently measurable.

In clinical use, it is desirable for such specimen collection containers to have rounded bottom configurations that closely simulate a standard-sized blood collection tube configuration instead of planar bottoms. Rounded bottom configurations facilitate compatibility with clinical equipment and instrumentation.

Therefore there is a need to provide a specimen collection container assembly for collecting blood samples and other biological fluid specimens of relatively small volumes where the assembly may be accommodated and/or compatible with standard clinical equipment and/or instrumentation and where the integrity of the sample and specimens are maintained during draw, storage and transport.

SUMMARY OF THE INVENTION

The present invention is a collection assembly comprising a container. The container preferably comprises an open top portion, a bottom portion and a sidewall extending from the open top portion to the bottom portion. The bottom portion comprises a closed bottom end. The sidewall comprises an inner wall, an outer wall and a wall space between the inner and outer wall. Most preferably, the wall space is formed during the molding process of the tube whereby an inert gas is injected into the sidewall so that a large amount of material can be eliminated and the inert gas is subsequently removed or exhausted from the sidewall. Optionally, the assembly may further comprise a closure at the open top portion of the container.

Most preferably, the wall space occupies an area within the sidewall of the container so as to reduce the interior volume of the container thereby creating a false volume effect to the container.

The wall space of the sidewall of the container provides a false volume effect to the assembly, as well as allowing the container to be compatible with standard clinical equipment and instrumentation because the external dimensions of the container are about the same as a standard-sized or full draw blood collection container assembly.

In addition, the assembly may further comprise a closure such as a cap or a stopper at the open end of the container.

Most preferably, the assembly of the present invention can be either evacuated or non-evacuated. Desirably, the assembly is made from polyethylene terephthalate, polypropylene, polyethylene, polyethylene napthalate polyvinyl chloride or copolymers thereof.

The assembly of the present invention is preferably formed as follows:

(a) melting a polymer such as polyethylene terephthalate (PET) or polypropylene;

(b) injecting the melted polymer into an injection mold that has a mold cavity of between 2–64 cavities;

(c) molding the melted polymer into a container that comprises an open top portion, a bottom portion and sidewall extending from the open top portion to the bottom portion whereby the sidewall comprises an outer wall that is formed by the mold cavity and inner wall that is defined by the core. As the skilled artisan will appreciate, injection molding is a process that works by putting the polymer in molten form and injecting same into a mold. The mold is a hollowed out area that allows the polymer to take shape after curing;

(d) injecting an inert gas into the sidewall of the container by a so-called core pin method, as utilized in molding operations for gas assist molding. The core pin method is a process which hollows out the thickness of the wall areas by taking up volume with gas instead of plastic. Thereafter, the gas is allowed to escape, which creates the pocket.

(e) ejecting the inert gas from the sidewall whereby a space is created between the inner and outer sidewall, creating the false volume of the tube;

(f) curing the tube, which takes place during the time the gas is ejected from the mold. Preferably, the curing time is between 6–15 seconds; and (g) ejecting the part from the mold by rods that push the part from the cavity.

An advantage of the assembly of the present invention is that it provides a full-draw blood collection container assembly having a reduced internal volume but with external dimensions that are approximately the same as a standard-sized blood collection container assembly. In addition, the assembly of the present invention has a standard draw rate as compared to partial draw rate tubes.

A further advantage of the assembly of the present invention is that it provides a specimen collection container which is universally compatible with various clinical equipment and instrumentation.

The assembly of the present invention may be easily handled by equipment configured to handle standard-sized blood collection tubes having standard external dimensions.

Most notably, is that the assembly of the present invention provides a blood collection container having full draw external dimensions but with a reduced internal volume as compared to standard-sized full draw blood collection tubes or standard-sized partial draw blood collection tubes.

Standard-sized full draw blood collection containers have an outer diameter of about 13 to about 16 millimeters, a length of about 75 to about 100 millimeters and an internal volume of about 6 to about 10 millimeters.

The assembly of the present invention therefore addresses the need for a full-draw low-volume blood collection container assembly that presents the external dimensions of a standard-sized blood collection tube.

The assembly of the present invention may be used to reliably collect small samples of blood or biological fluids and to maintain the integrity of the samples during storage and transport as compared to using standard-sized blood collection tubes. In addition, the assembly of the present invention can also be accommodated by standard-sized blood collection, transportation, storage, and diagnostic equipment. Furthermore, the assembly of the present invention may be used to reliably collect small samples of blood or biological fluids without being under partial pressure.

The assembly of the present invention is also compatible with existing instrumentation, labels, and bar code readers and obviates the need for new instrumentation and handling devices or procedures that would be required for smaller or varying sized tubes or tubes with flat planar bottoms.

DESCRIPTION OF THE DRAWINGS

FIG. 1 is a perspective view of a false bottom specimen tube of the prior art.

FIG. 2 is a longitudinal sectional view of the tube of FIG. 1 taken along line 2—2 thereof.

FIG. 5 is a perspective view of the assembly of the present invention.

FIG. 6 is a longitudinal sectional view of the assembly of FIG. 5 taken along line 6—6 thereof.

DETAILED DESCRIPTION

Figures 3, 4:
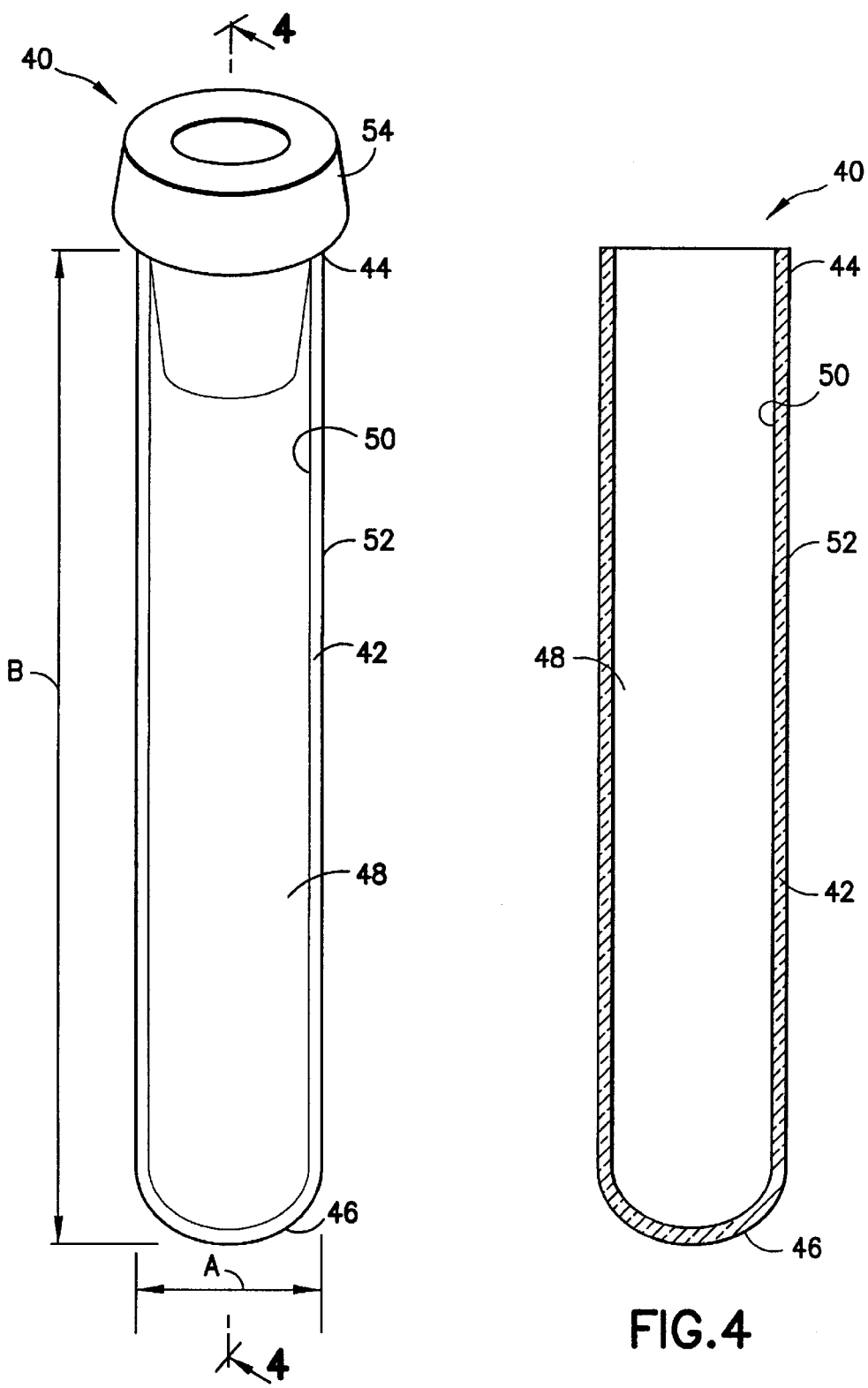
FIG. 3 is a perspective view of a standard-sized blood collection tube.
FIG. 4 is a longitudinal sectional view of the tube of FIG. 3 taken along line 4—4 thereof without the stopper.

The present invention may be embodied in other specific forms and is not limited to any specific embodiment described in detail which is merely exemplary. Various other modifications will be apparent to and readily made by those skilled in the art without departing from the scope and spirit of the invention. The scope of the invention will be measured by the appended claims and their equivalents.

Referring to the drawings in which like reference characters refer to like parts throughout the several views thereof, FIGS. 1 and 2 show a false bottom specimen container 10 of the prior art, having a sidewall 12 having an outer surface 14 and an inner surface 16. Sidewall 12 extends from an upper portion 18 to a lower portion 20. Upper portion 18 includes an open end 22 and a rim 24. Lower portion 20 comprises a closed bottom end 26. An annular skirt 28 extends from lower portion 20 and outer surface 14 to a flat planar bottom end 30 to define an open false bottom area 36. Interior volume 34 extends between rim 24 and closed bottom end 26.

Referring to the drawings in which like reference characters refer to like parts throughout the several view thereof, FIGS. 3 and 4 show a typical standard sized blood collection tube 40, having a sidewall 42 extending from an open end rim 44 to a closed end 46 and an interior area 48. Sidewall 42 has an inner wall surface 50 and an outer wall surface 52. Optionally, a closure 54 may be on the open end rim 44 of tube 40.

Tube 40 is most preferably a standard-sized blood collection tube having an outer diameter A of about 13–16 millimeters, a length B of about 75–125 millimeters and an internal volume 48 of about 6–10 milliliters as measured from rim 44 to closed end 46.

Interior area 48 is typically maintained at a lower-than-atmospheric internal pressure so that when a blood collection probe penetrates through the closure placing interior area 48 in communication with the circulatory system of a patient, the 48 will draw blood from the patient into the tube. Tube 40 may be described as a full-draw evacuated blood collection tube because the internal pressure of interior area 48 is low enough to draw a volume of blood substantially equal to the volume of interior area 48.

Referring to the drawings in which like reference characters refer to like parts throughout the several views thereof, FIGS. 5 and 6 show the preferred embodiment of the present invention, assembly 60. Assembly 60 comprises a container having an open end portion 110 and a closed end portion 112 whereby closed end portion 112 has a semi-spherical wall end 114.

Container 60 comprises a first cylindrical sidewall 82 at open end portion 110 having an outer surface 84 and an inner surface 86. First cylindrical sidewall 82 extends from a rim 85 towards a second cylindrical sidewall 90. Second cylindrical sidewall 90 comprises an outer surface 94, an inner surface 96 and a wall space 97 that extends between outer surface 94 and inner surface 96. A shoulder 92 connects inner surface 86 of first cylindrical sidewall 82 and inner surface 96 of second cylindrical sidewall 90. Second cylindrical sidewall 90 has a smaller internal diameter than first cylindrical sidewall 82. However, the external diameter of second cylindrical sidewall 90 is the same as the external diameter of first cylindrical sidewall 82. Second cylindrical sidewall 90 extends to semi-spherical wall end 114 of closed end portion 112.

An interior volume 106 of container 80 extends between rim 85 and semi-spherical wall end 114.

As shown in FIG. 5, assembly 60 has an outer diameter A of about 13 to 16 millimeters, a length B of about 75 to 100 millimeters, as measured from rim 85 to semi-spherical wall 112 of closed end portion. Interior volume 106 of container 80 can be about 1 to about 3 milliliters, as measured from rim 85 to semi-spherical wall end 114. It is within the purview of this invention that assembly 60 may have an outer diameter of about 13 to about 16 millimeters, a length of about 75 to about 100 millimeters and an interior volume of about 1 to about 3 milliliters.

Figure 7:
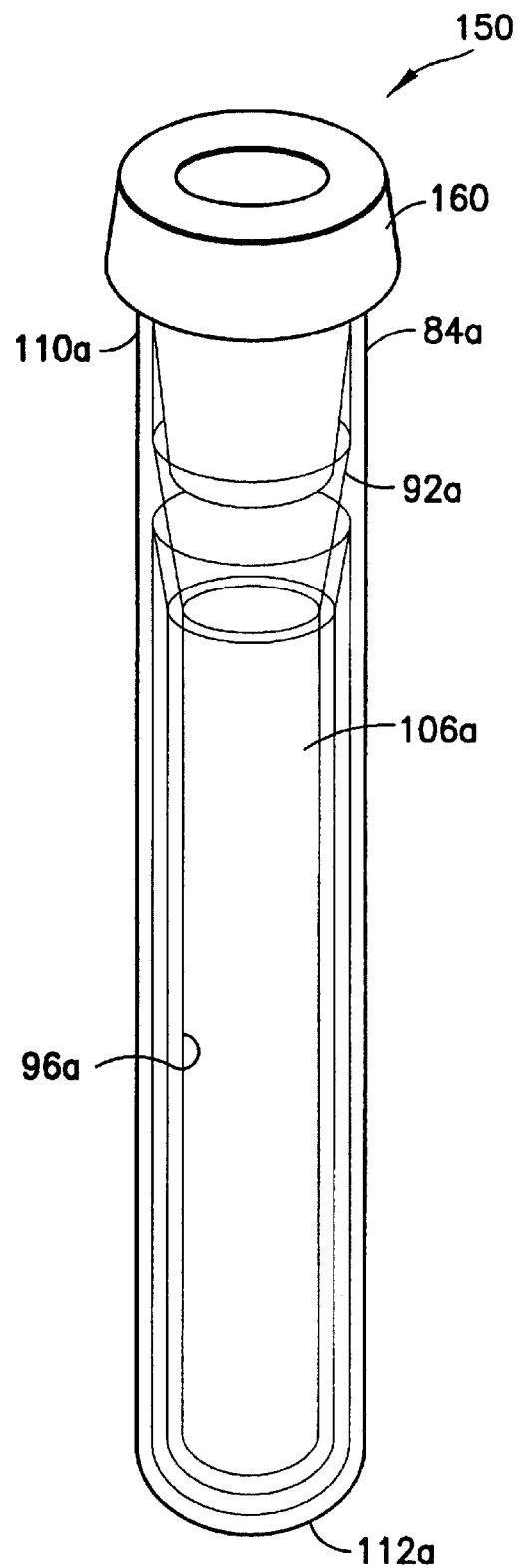
FIG. 7 is a perspective view of an alternate embodiment of the present invention.

The invention, as shown in FIG. 7 includes many components which are substantially identical to the components of FIGS. 5–6. Accordingly, similar components performing similar functions will be numbered identically to those components of FIGS. 5–6, except that a suffix "a" will be used to identify the similar components in FIGS. 7.

As illustrated in FIG. 7, a further embodiment of the invention is assembly 150 which includes a closure 160.

The embodiment of FIG. 7 may be evacuated or non-evacuated. When assembly 150 is evacuated, interior volume 106a is typically maintained at a lower-than-atmospheric internal pressure so that when a blood collection probe penetrates through the closure placing interior volume 106a in communication with the circulatory system of a patient, the lower-than-atmospheric pressure of interior volume 106a will draw blood from the patient into the tube. Assembly 150 may be described as a full-draw blood collection tube because the internal pressure of interior volume 106a is low enough to draw a volume of blood substantially equal to the volume of interior volume 106a.

The various embodiments of the present invention may be manufactured by known manufacturing methods including but not limited to injection molding with gas assistance. The preferred manufacturing method of the present invention is as follows:

(a) melting a polymer such as polyethylene terephthalate (PET) or polypropylene;

(b) injecting the melted polymer into an injection mold that has a mold cavity of between 2–64 cavities;

(c) molding the melted polymer into a container that comprises an open top portion, a bottom portion and sidewall extending from the open top portion to the bottom portion whereby the sidewall comprises an outer wall that is formed by the mold cavity and inner wall that is defined by the core. As the skilled artisan will appreciate, injection molding is a process that works by putting the polymer in molten form and injecting same into a mold. The mold is a hollowed out area that allows the polymer to take shape after curing;

(d) injecting an inert gas into the sidewall of the container by a core pin method, as utilized in molding operations for gas assist molding. The core pin method is a process which hollows out the thickness of the wall areas by taking up volume with gas instead of plastic. Thereafter, the gas is allowed to escape, which creates the pocket.

(e) ejecting the inert gas from the sidewall whereby a space is created between the inner and outer sidewall, creating the false volume of the tube;

(f) curing the tube, which takes place during the time the gas is ejected from the mold. Preferably, the curing time is between 6–15 seconds; and (g) ejecting the part from the mold by rods that push the part from the cavity.

What is claimed is:

1. A collection assembly comprising:

a plastic one-piece container comprising, an open top portion, a closed bottom portion and a sidewall extending from the top portion to the bottom portion, the sidewall comprising a single wall region and a double wall region integral with the single wall region, the double wall region comprising an inner wall, an outer wall, and a wall space between the inner wall and the outer wall, wherein the single wall region extends from the open top portion toward the closed bottom portion, and, at a location spaced from the open top portion, diverges into the inner wall and the outer wall of the double wall region, and wherein the inner diameter of the inner wall is smaller than the inner diameter of the sidewall at the single wall region.

2. The assembly of claim 1, further comprising a closure.

3. The assembly of claim 1, wherein said container is made from polyethylene terephthalate, polypropylene, polyethylene, polyethylene napthalate, polyvinyl chloride, or copolymers thereof.

4. The assembly of claim 1, wherein said container comprises a diameter of about 13 to about 16 millimeters, a length of about 75 to about 100 millimeters, and an interior volume of about 1 to about 3 millimeters.

5. The collection of assembly of claim 1, wherein the outer diameter of the outer wall is the same as diameter of the sidewall in the single wall region.

* * * * *